United States Patent [19]

Maggioni et al.

[11] 4,217,290

[45] Aug. 12, 1980

[54] PROCESS FOR PREPARING BIFUNCTIONAL ALIPHATIC ORGANIC COMPOUNDS

[75] Inventors: Paolo Maggioni, Cernusco Montevecchio; Francesco Mauri, Milan; Attilio Citterio, Monza, all of Italy

[73] Assignee: Brichima S.p.A., Milan, Italy

[21] Appl. No.: 50,331

[22] Filed: Jun. 20, 1979

[30] Foreign Application Priority Data

Jun. 26, 1978 [IT] Italy .................... 24744 A/78
Jun. 20, 1978 [IT] Italy .................... 24949 A/78

[51] Int. Cl.$^2$ .................. C09F 5/00; C11C 3/00; C11C 3/02; C07C 121/00; C07C 87/28

[52] U.S. Cl. .................... 260/404; 260/410; 260/410.9 R; 260/413; 260/465.4; 260/465.8 R; 260/561 R; 260/561 B; 260/561 K; 260/464; 560/174; 560/177; 560/180; 560/190; 560/155; 560/188; 560/193; 562/508; 562/509; 562/527; 562/582; 562/577; 562/578; 562/553; 562/590; 568/385; 568/412; 568/485; 568/494

[58] Field of Search ............ 260/404, 410 R, 410.9 R, 260/413 R, 465.4, 465.8, 593 A, 586 P, 561 R, 561 B, 561 K, 464, 601 R; 560/174, 177, 180, 190, 155, 188, 193; 562/508, 509, 527, 582, 577, 578, 553, 590

[56] References Cited

U.S. PATENT DOCUMENTS

| 2,624,764 | 1/1953 | Emerson et al. | 260/593 R |
|---|---|---|---|
| 2,671,810 | 3/1954 | Coffman | 260/593 A |
| 2,905,712 | 9/1959 | Braunwarth | 260/593 A |
| 3,928,452 | 12/1975 | Brunie et al. | 260/593 A |

FOREIGN PATENT DOCUMENTS

397505  9/1973  U.S.S.R. .................... 260/593 A

OTHER PUBLICATIONS

Billet, L. et al., Chem. Absts., vol. 82, 124753k (1975).
Schaafsma, S. et al., Chem. Absts., vol. 81, 37260h (1974).

*Primary Examiner*—John F. Niebling

[57] ABSTRACT

This invention consists of a process for preparing bifunctional aliphatic organic compounds of at least 6 carbon atoms, wherein a cycloaliphatic oxyhydroperoxide is reacted with an alpha-olefine having its double bond activated by a conjugate electron-attracting group, in the presence of a bivalent Cr salt, a bivalent V salt or a trivalent Ti salt.

7 Claims, No Drawings

PROCESS FOR PREPARING BIFUNCTIONAL ALIPHATIC ORGANIC COMPOUNDS

This invention relates to a new process for preparing bifunctional aliphatic organic compounds starting from cycloaliphatic oxyhydroperoxides. More precisely, this invention relates to a new industrially valid process for preparing linear or branched aliphatic compounds of at least six carbon atoms, comprising two equal or different functions chosen from the group consisting of —COOH, —CONH$_2$, —CN, —COOR, =CO, —CHO.

Compounds of the aforesaid type are widely used in the chemical industry, and particularly in the fields of synthetic fibres (polyamide, polyester), plastics, plasticisers, lubricating oils etc.

The importance of a process for simply and economically preparing a wide range of raw materials of the aforesaid type from commercially available products is therefore apparent.

The new process according to the present invention consists essentially of reacting a cycloaliphatic oxyhydroperoxide with an alpha-olefine having its double bond activated by a conjugate electron-attracting group, in the presence of a bivalent Cr salt, a bivalent V salt or a trivalent Ti salt. Schematically, the process is represented by the following equation:

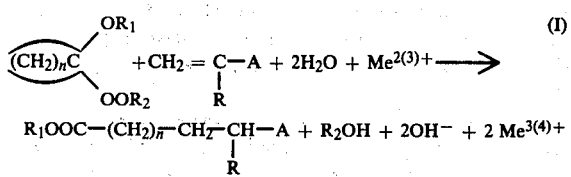

in which R$_1$ and R$_2$ are H, an alkyl of 1 to 6 carbon atoms, or a cycloalkyl of 3 to 7 carbon atoms, R is H, an alkyl of 1 to 6 carbon atoms, either simple or substituted by functional groups of any kind, or a functional group of any kind; A is an electron-attracting functional group chosen from the group consisting of —COOH, —COOR$_1$, —CN, —CONH$_2$, —CHO, =CO; n is a whole number from 2 to 6; Me is Cr, V or Ti.

In reality, the oxyhydroperoxides cannot generally be considered to be a pure product represented exclusively by formula (I), but are mostly a mixture of products, including dimers or trimers.

However, from the point of view of the reaction based on their transformation, oxyhydroperoxides act essentially in accordance with two formulas, one of which is that identified by (I), while the other is that identified hereinafter together with the reaction which it undergoes in the process according to the present invention:

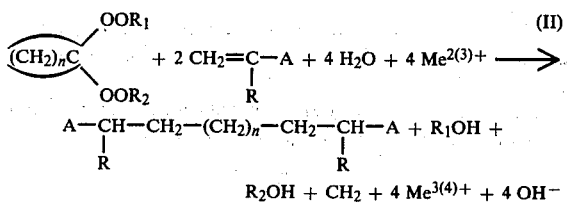

in which R$_1$, R$_2$, R, A, Me, n are as heretofore defined.

It can therefore be seen that the process according to the invention does not generally lead to a pure bifunctional aliphatic compound, but to a mixture of bifunctional products, one deriving from the addition of a single molecule of alpha-olefine to the oxyhydroperoxide, the other deriving from the addition of two molecules of alpha-olefine to one molecule of oxyhydroperoxide. These two products, which are equally important from a commercial aspect, are the only reaction products except for a limited percentage of aliphatic monocarboxylic acid deriving simply from opening the hydroperoxide ring in the presence of metal salts.

In practice, the relative proportions of the two compounds I and II and consequently the relative proportions of the monoaddition and biaddition products can be adjusted by adjusting the reaction conditions. It has in fact been found that the use of H$_2$O$_2$ at high concentration (exceeding 30%) or in excess displaces the equilibrium of the system towards the formation of the compounds II and consequently towards the biaddition product.

However, this equilibrium is not influenced in any way by the ratio of the two reagents, i.e. the oxyhydroperoxide and the activated alpha-olefine.

It is not however possible under industrially acceptable conditions to displace the equilibrium towards 100% of product II, whereas by acting in a deficiency of H$_2$O$_2$ in dilute solution, it is possible to obtain practically only compound I and consequently only the bifunctional monoaddition product.

The reaction temperature is 20° to 80° C.

Temperature influences this equilibrium in the sense that low temperatures favour the formation of compound II and consequently of biaddition products, whereas high temperature favour the formation of the monoaddition compound.

There are no problems in separating the two products produced in the form of a mixture, and which generally have different terminal functions and a different number of carbon atoms.

The reaction must be carried out in aqueous solution or in a solution of organic solvents such as methanol, ethanol, acetone, acetic acid, dimethylformamide or the like, in mixture with water.

The molar ratio of hydroperoxide to olefine lies between 0.1 and 1.

The excess olefine is recovered and recycled.

The excess olefine reduces the formation of the monocarboxylic acid, which is the only by-product of the new process, and is therefore a preferred condition.

The metal salts present, preferably chlorides or sulphates, clearly have a reducing action, and are used in stoichiometric quantity, i.e. in the proportion of 2 moles per mole of hydroperoxide.

Alternatively, they can be used in catalytic quantities in mixture with a reducing system which regenerates them by returning them continuously to the lower valency state, as the reaction proceeds.

The reducing system consists preferably of metals such as Al, Zn, Mn, Fe in aqueous solution acidified by strong acids, or by SO$_2$, sulphites, bisulphites etc.

A catalytic quantity means a quantity of metal salt less than the stoichiometric and down to a minimum of 0.1% of the stoichiometric.

The reducing system is used in at least stoichiometric proportion with respect to the Cr, V, Ti salt, but preferably in excess.

It should be noted that where catalytic quantities of Cr V or Ti are used, it is irrelevant whether the salt of these metals used is of minimum or maximum valency, as the reducing system returns it in any case to its minimum valency state.

The quantity of monocarboxylic acid produced in the reaction increases as the quantity of metal salts present increases, so that the use of the minimum catalytic quantity (compatible with the reaction velocity) of the metal salt is a preferred condition.

The hydroperoxides which represent the starting materials for the process according to the invention are preferably prepared by oxidising the corresponding alicyclic ketones with $H_2O_2$ or with hydroperoxides.

It should be noted that although the reaction proceeds equally well with $H_2O_2$ and hydroperoxides in which $R_1$ and $R_2$ are other than hydrogen and as heretofore defined, in practice if it is required to operate with cycloaliphatic oxyhydroperoxides in which $R_1$ and $R_2$ are other than hydrogen, it is always preferable to oxidise the alicyclic ketone with $H_2O_2$ in the presence of alcohols of formula $R_1OH$.

The preferred cycloaliphatic ketone is cyclohexanone.

Alternatively, the oxyhydroperoxides can be prepared by auto-oxidation of the corresponding alcohol of ether according to the equations:

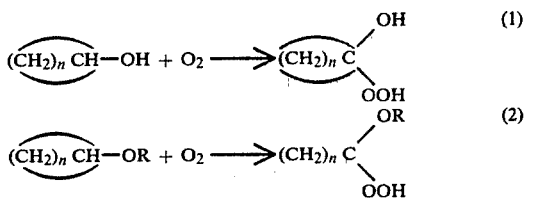

The reaction represented by these equations can be carried out by simply agitating the alcohol or ether considered, at a temperature of 40° to 100° in the presence of a small quantity of peroxide as initiator, or by photo-chemical activation.

However, the preferred process is that starting from ketones, and is carried out in aqueous solution at ambient temperature in the presence of a strong acid.

The preferred activated olefine compounds are the vinyl compounds of formula $CH_2=CHD-A$ in which A has the aforesaid meaning.

It is apparent that the starting ketone and vinyl compounds are chosen in relation to the bifunctional compounds which it is required to prepare, and the carbon atoms contained therein.

The industrial interest in the process is particularly related to the possibility of obtaining long chain aliphatic amines and aliphatic dicarboxylic acids, these being products widely used in the synthetic fibre and plastics fields.

A process for preparing said bifunctional compounds which is truly economical on an industrial scale has not been known up to the present time.

It must be emphasised that the new process enables practically any bifunctional aliphatic compound to be prepared, both by suitably choosing the starting cycloaliphatic ketone and vinyl compound (number of carbon atoms, possible side chains, functional groups present therein), and by further transformation of the bifunctional compounds initially obtained (etherification, esterification, oxidation, reduction, hydrolysis).

In order to facilitate reproduction of the present process, some examples are given by way of example, which however obviously are non-limiting due to the vastness of the class of compounds obtainable and the substantial identity of the process with any cycloaliphatic ketone and with any alpha-olefine as yet prepared.

EXAMPLE 1

20 g of cyclohexanone and 23 ml of 30% hydrogen peroxide are mixed under agitation at ambient temperature in the presence of 1 ml of an aqueous solution of concentrated hydrochloric acid. The mixture is dissolved in 20 ml of acetic acid and is dripped under agitation at 25° C. into a mixture of 8 g of $CrCl_3$, 10 g of zinc dust and 20 g of acrylonitrile in 115 ml of acetic acid and 35 ml of an aqueous solution of concentrated hydrochloric acid. The acetic acid, the excess acrylonitrile and 3 g of cyclohexanone are recovered by distillation. The residue is extracted with ether, and the acid part is separated from the neutral part by a 10% soda solution. The acid part consists of two products: 7 g of hexanoic acid which are separated by distillation, and 14.5 g of 8-cyano-octanoic acid.

The neutral product consists of 7 g of 1,9-dicyanononane.

Yield of useful products with respect to $H_2O_2$ 80%.
Yield with respect to cyclohexanone 72%.

EXAMPLE 2

20 g of cyclohexanone and 46 ml of 15% $H_2O_2$ are mixed under agitation at ambient temperature in the presence of 1 ml of an aqueous solution of concentrated HCl.

The process is carried out as in the previous example, finally extracting the residue with ether and separating the acid part from the neutral part by means of a soda solution.

In this case the following are obtained: hexanoic acid 6.8 g 8-cyanooctanoic acid 16.1 g 1,9-dicyanononane 4.2 g In this case there has thus been a considerable increase in the quantity of 8-cyanooctanoic acid produced, at the expense of the 1,9-dicyanononane.

Yield of useful products with respect to $H_2O_2$ 70.1%.
Yield with respect to cyclohexanone 58.2%.

EXAMPLE 3

20 g of cyclohexanone and 20 ml of 60% $H_2O_2$ are mixed under agitation at ambient temperature in the presence of 1 ml of an aqueous solution of concentrated HCl.

The process is carried out as in Example 1, finally extracting the residue with ether and separating the acid part from the neutral part by a soda solution.

In this case the following are obtained: hexanoic acid 5.1 g 8-cyanooctanoic acid 12.6 g 1,9-dicyanononane 11.2 g There is thus a considerable increase in the quantity of 1,9-dicyanononane at the expense of the 8-cyanooctanoic acid.

Yield of useful products with respect to $H_2O_2$ 49.3%
Yield with respect to cyclohexanone 67.4%.

EXAMPLE 4

The process described in Example 1 was repeated exactly, but using 40 g of acrylonitrile.

In this case the following products were obtained: hexanoic acid 3.1 g. 8-cyanooctanoic acid 16.3 g 1,9-dicyanononane 8.1 g The production of hexanoic acid was therefore considerably decreased.
Yield with respect to $H_2O_2$ 92.3%.
Yield with respect to cyclohexanone 69.6%.

EXAMPLE 5

The process of Example 1 was repeated, but this time working at 80° C.
The following were obtained: hexanoic acid 7.1 g 8-cyanooctanoic acid 14 g 1,9-dicyanononane 5.8 g with an obvious increase in the yield of 8-cyanooctanoic acid.
Yield with respect to $H_2O_2$ 73%.
Yield with respect to cyclohexanone 56.6%.

EXAMPLE 6

The process of Example 1 was repeated, but using a catalytic system consisting of 6 g of $Vo(SO_4)_2$ and 5 g of aluminium.
The following products were obtained: 8-cyanooctanoic acid 14.2 g 1,9-dicyanononane 6.8 g
Yield with respect to $H_2O_2$ 78%.
Yield with respect to cyclohexanone 70%.
It is apparent that the change in the catalytic system did not substantially influence the progress of the reaction.

EXAMPLE 7

The process of Example 1 was repeated, but using a catalytic system consisting of 7 g of $TiCl_3$ and 10 g of Fe.
The following products were obtained: 8-cyanooctanoic acid 13.9 g 1,9-dicyanononane 7.1 g
Yield with respect to $H_2O_2$ 79%.
Yield with respect to cyclohexanone 70%.
Again in this case, the change in catalytic system, other conditions being equal, has substantially no influence on the progress of the reaction.

EXAMPLE 8

20 g of cyclohexanone and 23 ml of 30% $H_2O_2$ are mixed under agitation at ambient temperature in the presence of 1 ml of an aqueous solution of concentrated HCl.
The mixture is dissolved in 20 ml of acetic acid and is then dripped under agitation at a temperature of 20° C. into a mixture containing 68 g of $CrCl_2$, 20 g of acrylonitrile in 80 ml of acetic acid and 20 ml of an aqueous solution of concentrated hydrochloric acid. The temperature rises to 60° during the addition.
The acetic acid, the excess acrylonitrile and the unreacted cyclohexanone are recovered by distillation.
The residue is extracted with ether, and the acid part is separated from the neutral part by means of a 10% soda solution.
The following are obtained: hexanoic acid 9.3 g 8-cyanooctanoic acid 11.2 g 1,9-dicyanononane 5.8 g.
Yield with respect to $H_2O_2$ 64.8%.
Yield with respect to cyclohexanone 48.3%.
It is apparent that the presence of large quantities of metal salt favours the formation of the hexanoic acid by-product.

EXAMPLE 9

20 g of cyclohexanone and 23 ml of 30% hydrogen peroxide are mixed under agitation at ambient temperature in the presence of 1 ml of an aqueous solution of concentrated hydrochloric acid.
The resultant mixture is dissolved in 20 ml of methanol and is allowed to drip under agitation at 25° into a mixture containing 8 g of $CrCl_3$, 5 g of Al powder and 20 g of acrylonitrile in 80 ml of methanol and 20 ml of an aqueous solution of concentrated hydrochloric acid.
The methanol is evaporated and the excess acrylonitrile, 5 g of cyclohexanone and 6.7 of methylhexanoate are recovered. 18.1 g of the methyl ester of 8-cyanooctanoic acid and 5.2 g of 1,9-dicyanononane are extracted from the residue by ether.
Yield of useful products with respect to $H_2O_2$ 77.5%.
Yield with respect to cyclohexanone 83.7%.

EXAMPLE 10

10 g of cyclohexanone and 14 ml of 30% hydrogen peroxide are mixed under agitation at ambient temperature in the presence of 0.5 ml of an aqueous solution of concentrated hydrochloric acid.
The resultant mixture is dripped between 20° and 60° C. under agitation into a mixture of 3 g of $CrCl_3$, 4 g of zinc dust and 20 g of acrylic acid in 60 ml of a 5% aqueous solution of hydrochloric acid. The solution is extracted with ethyl acetate, and the following are obtained from the extract:
1,9-nonandioic acid 7.6 g
1,11-undecandioic acid 3.2 g
Yield of useful products with respect to $H_2O_2$ 69%.
Yield with respect to cyclohexanone 54.1%.

EXAMPLE 11

The process is carried out as in Example 1, but using 32 g of methyl acrylate instead of the acrylonitrile.
The reaction mixture is extracted with ethyl acetate.
The following are obtained from the extract:
methyl semiester of 1,9-nonadionic acid 13.8 g
methyl diester of 1,11-undecandioic acid 6.6 g
Yield with respect to $H_2O_2$ 58.1%.
Yield with respect to cyclohexanone 44.6%.

EXAMPLE 12

The process is carried out as in Example 1 but using 25 g of acrylamide instead of the acrylonitrile. 14.7 g of the monoamide of 1,9-nonandioic acid and 7.2 g of the diamide of 1,11-undecandioic acid are obtained.
The reaction mixture is extracted with chloroform.
The following are obtained from the extract:
monoamide of 1,9-nonandioic acid 14.7 g
diamide of 1,11-undecandioic acid 7.2 g
Yield with respect to $H_2O_2$ 70%.
Yield with respect to cyclohexanone 54%.

EXAMPLE 13

The process is carried out as in Example 1 but using 25 g of methylvinylketone instead of the acrylonitrile.
The reaction mixture is extracted with ethyl acetate.
The following are obtained from the extract:
9-ketodecanoic acid 13.1 g
2,12-diketotridecane 5.2 g
Yield of useful products with respect to $H_2O_2$ 65%.
Yield with respect to cyclohexanone 49%.

EXAMPLE 14

6 g of the alpha-hydroperoxide of dicyclohexylether, prepared by treating dicyclohexylether with 30% $H_2O_2$, are added under agitation at 25° C. to a mixture of 0.8 g of $CrCl_3$, 1 g of Zn dust and 2 g of acrylonitrile in 8 ml of acetic acid and 2 ml of an aqueous solution of concentrated HCl.

The acetic acid and excess acrylonitrile are distilled off, and the following are extracted from the residue by ethyl acetate:

cyclohexylhexanoate 2 g.
cyclohexylester of 8-cyanooctanoic acid 3.5 g
Yield with respect to the hydroperoxide 49.7%.

What we claim is:

1. A process for preparing bifunctional aliphatic organic compounds of at least 6 carbon atoms, wherein a cycloaliphatic oxyhydroperoxide is reacted with an alpha-olefine having its double bond activated by a conjugate electron-attracting group, in the presence of a bivalent Cr salt, a bivalent V salt or a trivalent Ti salt, at a temperature of 20° to 80° C. in water or in an aqueous organic solvent.

2. A process as claimed in claim 1, wherein the electron-attracting group which activates the double bond is chosen from the group consisting of —COOH, —COOR, —CONH, —CN, —CHO, =CO.

3. A process as claimed in claim 1, wherein the bivalent CR, bivalent V or trivalent Ti salt is used in stoichiometric proportion with respect to the oxyhydroperoxide.

4. A process as claimed in claim 1, wherein the bivalent Cr, bivalent V or trivalent Ti salt is used in catalytic quantity, down to a minimum of 0.1% of the stoichiometric, in the presence of a reducing system which continuously regenerates its valency state.

5. A process as claimed in claim 4, wherein the bivalent Cr, bivalent V or trivalent Ti salt is replaced wholly or partly by a higher valency salt of the same metal.

6. A process as claimed in claim 4, wherein the reducing system is chosen from the group consisting of metals in an acid solution, or in a solution acidified by $SO_2$, sulphites or bisulphites.

7. A process as claimed in claim 1, characterised in that the ratio of cycloaliphatic oxyhydroperoxide to olefine lies between 0.1 and 1.

* * * * *

UNITED STATES PATENT AND TRADEMARK OFFICE
CERTIFICATE OF CORRECTION

PATENT NO. : 4,217,290
DATED : August 12, 1980
INVENTOR(S) : Paolo Maggioni, Francesco Minisci, Attilio Citterio It is certified that error appears in the above-identified patent and that said Letters Patent are hereby corrected as shown below:

Abstract and Title Page:

Under Item [75] Inventors:

Cancel "Mauri" and substitute --Minisci--

Signed and Sealed this

Thirty-first Day of May 1983

[SEAL]

Attest:

DONALD J. QUIGG

*Attesting Officer*  *Acting Commissioner of Patents and Trademarks*